United States Patent
Lacoste et al.

(10) Patent No.: US 7,713,203 B2
(45) Date of Patent: May 11, 2010

(54) ULTRASOUND TREATMENT DEVICE AND METHOD

(75) Inventors: François Lacoste, Paris (FR); Jean-Yves Chapelon, Villeurbanne (FR); Olivier Pichot, Corenc (FR); René Milleret, Montpellier (FR); Samuel Pichardo, Lyons (FR)

(73) Assignee: Inserm and Theraclion, Paris (FR)

(*) Notice: Subject to any disclaimer, the term of this patent is extended or adjusted under 35 U.S.C. 154(b) by 301 days.

(21) Appl. No.: 11/572,465

(22) PCT Filed: Jul. 19, 2005

(86) PCT No.: PCT/FR2005/001842

§ 371 (c)(1),
(2), (4) Date: Jan. 22, 2007

(87) PCT Pub. No.: WO2006/021651

PCT Pub. Date: Mar. 2, 2006

(65) Prior Publication Data

US 2008/0194955 A1    Aug. 14, 2008

(30) Foreign Application Priority Data

Jul. 23, 2004  (FR) .................. 04 08180
Aug. 13, 2004  (FR) .................. 04 08874

(51) Int. Cl.
    *A61B 8/14* (2006.01)
    *A61B 5/00* (2006.01)
    *G01N 29/00* (2006.01)

(52) U.S. Cl. ............... 600/439; 73/633; 601/2

(58) Field of Classification Search .............. 600/439, 600/444, 445, 447, 459–467; 310/335; 73/606, 73/619–633
See application file for complete search history.

(56) References Cited

U.S. PATENT DOCUMENTS

| 3,958,559 | A | * | 5/1976 | Glenn et al. ................. 600/472 |
| 4,384,231 | A | * | 5/1983 | Ishikawa et al. ............. 310/335 |
| 4,459,852 | A |   | 7/1984 | Chubachi et al. |
| 4,641,530 | A | * | 2/1987 | Attal et al. .................... 73/606 |
| 4,938,216 | A | * | 7/1990 | Lele .............................. 601/3 |
| 5,230,334 | A |   | 7/1993 | Klopotek |
| 5,640,961 | A | * | 6/1997 | Verdonk ....................... 600/459 |
| 5,762,066 | A |   | 6/1998 | Law et al. |
| 6,083,159 | A |   | 7/2000 | Driscoll, Jr. et al. |

(Continued)

FOREIGN PATENT DOCUMENTS

GB    2113099 A    8/1983

(Continued)

*Primary Examiner*—Eric F Winakur
*Assistant Examiner*—Lawrence N Laryea
(74) *Attorney, Agent, or Firm*—Marsh Fischmann & Breyfogel LLP (57) ABSTRACT

The inventive ultrasound treating device comprises a first processing transducer set (11) for transmitting a beam of high-intensity ultrasound waves to a treatable area (3), wherein said beam comprises an aspheric wavefront and forms a focal spot (6) on the treatable area elongated and inclined with respect to the direction of the ultrasound wave propagation and the focal spot (6) length is less than the length of the transducer (11). The inventive device is particularly suitable for treating an elongated area such as vein portions enveloping a pathological valve.

22 Claims, 6 Drawing Sheets

U.S. PATENT DOCUMENTS

| | | |
|---|---|---|
| 6,206,843 B1 | 3/2001 | Iger et al. |
| 6,374,132 B1 | 4/2002 | Acker et al. |
| 6,398,777 B1 | 6/2002 | Navarro et al. |
| 6,436,061 B1 | 8/2002 | Costantino |
| 6,613,045 B1 | 9/2003 | Laufer et al. |
| 6,656,136 B1 | 12/2003 | Weng et al. |
| 6,676,601 B1 | 1/2004 | Lacoste et al. |
| 2006/0058664 A1 * | 3/2006 | Barthe et al. ................ 600/439 |

FOREIGN PATENT DOCUMENTS

| | | |
|---|---|---|
| WO | 0102055 A1 | 1/2001 |
| WO | 0117455 A2 | 3/2001 |
| WO | 0134018 A2 | 5/2001 |

* cited by examiner

ULTRASOUND TREATMENT DEVICE AND METHOD

TECHNICAL FIELD

The present invention relates to an ultrasound treatment device and an ultrasound treatment method, in particular for the treatment of varicose veins.

The venous system comprises a deep intramuscular network and a superficial sub-cutaneous network which ensures, in a parallel manner, the return of the venous blood. In these two networks, the venous hemodynamics depends on different mechanisms which generate a pressure gradient allowing the venous blood to be driven and drawn towards the right atrium and ventricle. At the level of the lower limbs, despite a pressure gradient which is low and variable according to the physiological conditions, the venous return remains effective under all circumstances thanks to the existence of valves arranged in all the veins of the lower limbs, which constitute authentic anti-reflux devices.

Figure 1A:
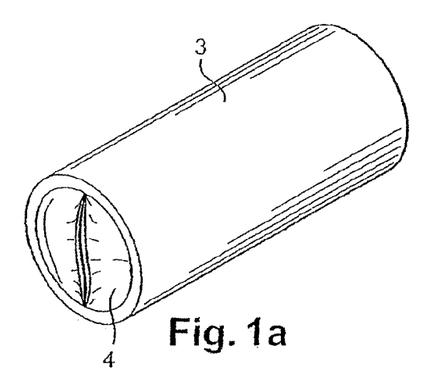
FIGS. 1a and 1b, diagrammatic views, respectively in perspective and in section, of a healthy vein.
Figure 1B:
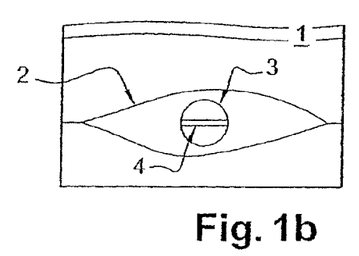

FIGS. 1a and 1b illustrate a healthy vein. The vein 3 is illustrated with a healthy valve 4 with leaves closing together edge to edge in order to produce the blood anti-reflux function. The vein 3 of the superficial network is situated in a fascia 2 under the skin 1.

The varices, which characterize superficial venous disease, are associated with the superficial venous network of the lower limbs. This pathology manifests itself at the morphological level by an abnormal increase in the calibre of the vein and at the hemodynamic level by the existence of a reflux linked to a dysfunctioning of the venous valves.

Figure 2A:
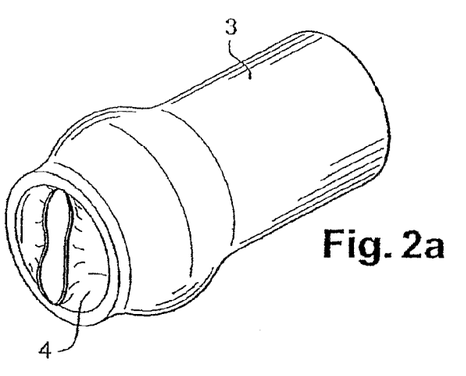
FIGS. 2a and 2b, diagrammatic views, respectively in perspective and in section, of a varicose vein.
Figure 2B:
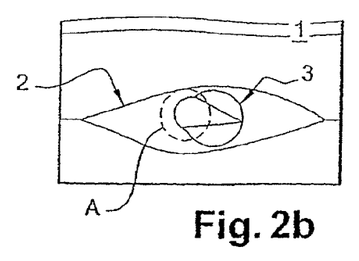

FIGS. 2a and 2b illustrate a varicose vein. The vein 3 is illustrated with a pathological valve 4 with leaves which do not close completely. The blood anti-reflux function is therefore no longer completely ensured. A dehiscent portion A then appears on the wall of the vein 3 inside the fascia 2.

Even if knowledge about the origin and the nature of varicose disease is still limited, the hypothesis of a primitive impairment of the vein wall is currently accepted. The exploration of the superficial venous network of the lower limbs by Doppler ultrasonography greatly advanced knowledge in this field. Thanks to this technique it is possible to study the calibre of the diseased vein and measure the reflux, but also identify the pathological valves and study the characteristics of the reflux of the varicose vein in a precise manner.

STATE OF THE ART

Standard therapeutic treatments are based on the surgical exeresis of pathological veins.

Recently a conservative treatment was tested for an early stage of superficial venous insufficiency. Usually in the initial stage of varicose disease a dilatation of the vein wall can be observed at the level of the insertion rings of the preterminal valve (situated at the top of the thigh) and the valve of the femoral canal (at the bottom of the thigh). Restoring the competence of these valves makes it possible, in 90% of cases where the use of this treatment is possible, to limit subsequent development towards varicose venous insufficiency. The only therapeutic technique carried out for this purpose which is currently available is surgical. This is reconforming by external stenting, which consists in surrounding the dilated venous segment with a ring of Teflon or silicone in order to reduce its calibre until the proper operation of the valve is restored. Such a treatment was described in the publication "The treatment of varicose veins with external stenting to the Saphenofemoral junction" by R J. Lane, M. L. Cuzzilla and J. C. Coroneos, Vasc. Endovasc. Surg. 36, 2002, pp 179-192.

Another known treatment is sclerotherapy, which consists of the injection into the vein of a sclerosing product. This treatment technique is however difficult to control.

Other treatments use heat, either to coagulate the blood situated in the vein and thus obtain a thrombosis, or to reduce or block the diameter of the vein. These treatments firstly cause the obliteration of the portion of varicose vein, then its fibrosis and its lysis by macrophages. Control ultrasonographs at 18 months show a total disappearance of the pathological vein wall. For example the so-called "closure" system described in the U.S. Pat. No. 6,613,045, developed by the company VNUS, uses radiofrequencies in order to heat the portion of varicose vein. Another system described in the U.S. Pat. No. 6,398,777 uses heat provided by a laser.

Other treatments have been proposed which use heat provided by ultrasound.

For example, the publication by Delon-Martin et al "Venous thrombosis generation by means of high intensity focused ultrasound", Ultrasound in Med and Biol, 1995, 21 (1), p 113-119, describes tests with power ultrasound. The ultrasound is focussed in the vein however, the aim being to coagulate the blood and not the venous or peripheral tissue.

Moreover, the publication by Schultz-Haakh et al "Ultrasonic Treatment of Varicose Veins", Angiology. February 1989, 40 (2), p 129-137 describes destruction of the venous wall with focussed ultrasound. Juxtaposed ultrasound shots are applied in order to destroy the wall in order to produce the occlusion of the vein.

The U.S. Pat. No. 6,436,061 describes a method consisting in heating the tissue situated between the vein and the skin. This document also proposes destroying the endothelium of the vein in order to generate secondary thromboses. Although the authors recognize that the origin of the disease is the malfunctioning of the valves, they do not act on these or on the vein itself, but on the contrary they seek to obliterate the vein completely.

The U.S. Pat. No. 6,083,159 describes a method for the coagulation of blood by the application of focussed ultrasound. The method described in this document does not envisage treating the valves.

The U.S. Pat. No. 6,676,601 proposes aiming at a target to be coagulated using an integral transducer operating in Doppler mode.

The U.S. Pat. No. 5,230,334 describes the application of focussed high-frequency ultrasound (>20 MHz) in order to contract the collagen present in the cornea. It is recommended not to heat to more than 60-70° C. and to limit the heat exposure to a few seconds. However, no correct combinations of acoustic parameters are given (frequency, power, intensities, exposure time) in order to make it possible to effectively retract the cornea without collateral damage.

Moreover, the devices with high-intensity focussed ultrasound, known by the name HIFU (or "High Intensity Focused Ultrasound") generally comprise a therapy transducer transmitting a spherical wavefront, so that the acoustic energy is concentrated in a punctiform spot. If it is sought to treat a line or a volume of tissue, it is necessary to move the focal point by means of a mechanical movement of the transducer or an electronic movement of the focal point.

The patents U.S. Pat. No. 6,656,136 and U.S. Pat. No. 5,762,066 envisage the use of transducers transmitting aspherical wavefronts, so as to enlarge the focal point. These documents do not however envisage the use of surfaces allowing the production of a very fine line, of a given length.

The U.S. Pat. No. 4,938,216 proposes using a transducer transmitting a cylindrical wavefront so as to produce an elongated focal spot substantially equal to the length of the transducer. The acoustic concentration of such a transducer is however limited.

SUMMARY OF THE INVENTION

A need therefore exists for an ultrasound treatment device which makes it possible to treat a target having the shape of a line segment, such as a varicose vein wall for example.

A need also exists for an ultrasound treatment method for a given area, for example a varicose vein, which can be implemented by transcutaneous route at an early stage of the pathology.

For this purpose, the invention proposes an ultrasound device comprising a first treatment transducer which can transmit a beam of ultrasound waves to an area to be treated, the beam having an aspherical wavefront and creating a focal spot on the area to be treated which is elongated and inclined with respect to the direction of propagation of the ultrasound waves, the length of the focal spot being less than the length of the transducer.

According to one characteristic, the focal spot is perpendicular to the direction of propagation of the ultrasound waves.

According to one characteristic, the device also comprises a second imaging transducer capable of displaying the area to be treated.

According to the embodiments, the imaging transducer is able to display a plane perpendicular to a major axis of the focal spot or a plane inclined with respect to the major axis of the focal spot.

According to the embodiments, the treatment transducer transmits a wavefront with a conical shape or an ellipsoid shape; or with a spherical shape combined with a lens which is cylindrical or has a flat shape combined with an elliptical lens.

According to another embodiment, the treatment transducer transmits a wavefront defined as the envelope of a plurality of circles respectively centred on a plurality of points of the focal line and connected to each other in such a way that the two normals at each point of the envelope intersect the focal line.

According to one embodiment, the treatment transducer is separated into a plurality of independent parts which are each able to transmit ultrasound waves at the same frequency and phase shifted between themselves so as to form an aspherical wavefront.

According to one embodiment, the device comprises a plurality of treatment transducers which are able to focus ultrasound waves in the same focal spot on an area to be treated.

According to one embodiment, the imaging transducer is integral with the treatment transducer.

According to one characteristic, the device also comprises means for controlling the frequency and/or the power of the ultrasound waves transmitted by the first treatment transducer and/or the duration of transmission of the ultrasound waves on the surface to be treated.

According to one characteristic, the control means are able to interpret data provided by the imaging transducer.

The invention thus relates to an ultrasound device comprising a first treatment transducer which is able to transmit a beam of ultrasound waves to an area to be treated, the beam having an aspherical wavefront, other than cylindrical, and creating a focal spot on the area to be treated which is elongated and inclined with respect to the direction of propagation of the ultrasound waves.

The invention also relates to a method for the transmission of ultrasound onto an area to be treated comprising the stages of:
  transmission of a beam of ultrasound waves having an aspherical wavefront by a treatment transducer;
  focussing of the ultrasound waves according to an elongated focal spot shorter than the length of the transducer and inclined with respect to the direction of propagation of the ultrasound waves.

According to one characteristic, the method also comprises a stage of locating the area to be treated by Doppler ultrasonography.

According to one characteristic, the method also comprises a stage of displaying the treated area.

According to one embodiment, the stages of transmission and/or focussing of the ultrasound waves are monitored by displaying the treated area.

The invention also relates to the device according to the invention for its use for the treatment of a vein wall or for the treatment of a solid tumour.

Moreover, the invention also relates to a method for the therapeutic treatment of an area of the human body, comprising the stages of:
  locating the area to be treated,
  transmission of a beam of ultrasound waves to the area to be treated by a treatment transducer, the beam having an aspherical wavefront;
  focussing of the ultrasound waves according to an elongated focal spot shorter than the length of the transducer and inclined with respect to the direction of propagation of the ultrasound waves.

According to the applications of the therapeutic method of the invention, the area to be treated is a vein wall or a solid tumour.

The invention also relates to a method for the therapeutic treatment of a pathological vein by heating of the vein wall with focussed ultrasound.

According to one embodiment, heating of the vein wall is carried out at the level of an insertion ring for a valve.

BRIEF DESCRIPTION OF THE FIGURES

Other characteristics and advantages of the invention will become apparent on reading the following detailed description of the embodiments of the invention, given by way of example only and with reference to the drawings which show.

DETAILED DESCRIPTION OF THE EMBODIMENTS OF THE INVENTION

The ultrasound treatment device according to the invention comprises a first treatment transducer which is able to transmit a beam of ultrasound waves, for example high-intensity ultrasound waves (HIFU), to an area to be treated. The area to be treated can be, for example, a varicose vein.

The treatment transducer transmits a beam of waves having an aspherical wavefront and creating a focal spot on the area to be treated which is elongated and inclined with respect to the direction of propagation of the ultrasound waves.

The focal spot is defined, in a manner known per se, as an area of concentration of the ultrasound waves on a surface with a concentration greater than a given threshold.

The direction of propagation can be defined as the vector sum of the directions of the rays of the beam of waves, weighted by the intensity. Thus, in the case of iso-intensity rays, the direction of propagation corresponds to the mean of the directions of the rays of the beam of waves.

The wavefront is defined as the equiphase surface of the wave transmitted. The wavefront transmitted by the treatment transducer is such that its focal spot is elongated. An elongated spot is thus defined as a spot having one dimension greater than the others. Thus, the width of the focal spot is essentially limited by diffraction whereas the length of the spot corresponds to several times its diffraction width, at least three or four times. The depth of the focal spot is limited by the penetration of the waves in a manner known per se.

The length of the focal spot is less than the length of the transducer. Thus, there is an improved concentration of the focussed ultrasound power compared to a focal line obtained with a standard cylindrical transducer. The transducer according to the invention has a surface as wide and as long as possible in order to concentrate as much as possible the beam of ultrasound waves transmitted.

The device according to the invention is therefore particularly suitable for the treatment of an elongated area, such as portions of veins surrounding the attachment point of a pathological valve.

In the following description, the words length, width, thickness, are used to refer to the vein constituting the area to be treated represented in the figures. These positioning references are illustrative and should not be understood as limiting the position of the device in operation.

Similarly, the following description refers to an area to be treated constituted by a portion of varicose vein, but it is understood that this is only an illustrative example and that the device and the method according to the invention are applicable to any other area to be treated, such as for example a solid tumour, for example in the breast, the prostate, or the thyroid gland.

Thus a treatment transducer is defined as a transducer which is able to transmit a beam of waves with an intensity, a frequency and a duration such that the properties of the target can be modified by the application of the beam. Moreover, an imaging transducer is defined as a transducer which is able to transmit a beam of waves with an intensity and a frequency such that the properties of the target cannot be modified by the application of the beam.

Figure 3:
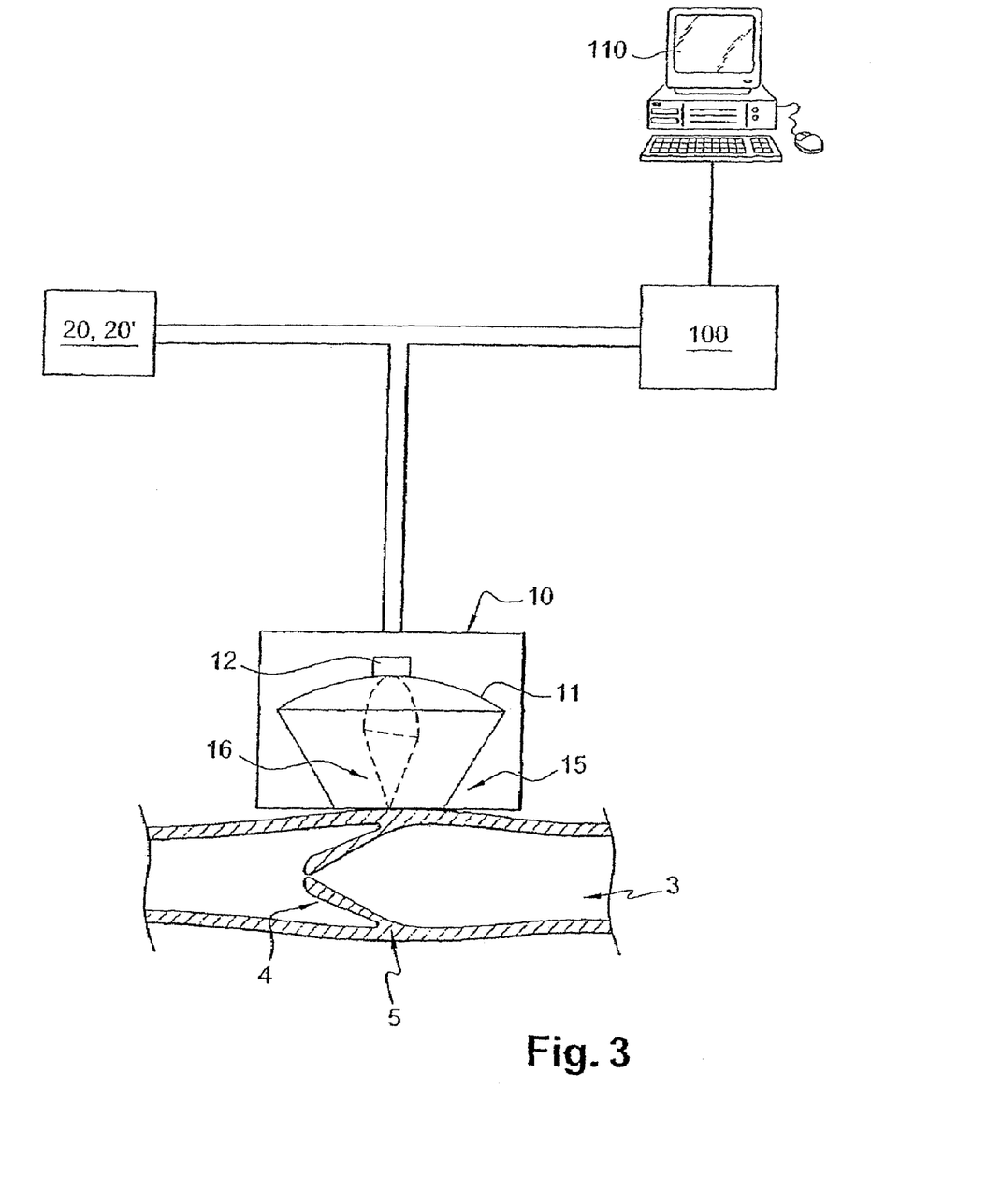
FIG. 3, a diagrammatic view of an ultrasound treatment device according to the invention.

FIG. 3 diagrammatically illustrates an ultrasound treatment device according to the invention.

The device according to the invention comprises a probe 10 integrating at least one treatment transducer 11 transmitting a beam of ultrasound waves having an aspherical wavefront. The treatment transducer 11 is able to transmit a beam of high-intensity focussed ultrasound waves with a high power concentration of the order of 1 KW/cm$^3$. The probe 10 can also integrate an imaging transducer 12, for example an ultrasonograph transducer, known per se.

The probe 10 is intended to be placed facing an area to be treated. In the example illustrated, the area to be treated is constituted by a varicose vein 3. The probe 10 can be placed against the skin at the level of the insertion rings of a pathological valve 4. The probe must have a reduced bulk in order to allow the clinician to easily identify the target area at any time.

According to the invention, the treatment transducer 11 is able to focus the ultrasound waves in the plane 15 of the vein according to a focal spot elongated along the length of the vein 3. The imaging transducer 12 can be placed in such a way as to display the vein in a plane perpendicular 16 to it. This arrangement is not obligatory although it is preferable since it allows better viewing by an ultrasonographic effect of the whole width of the vein and its valve.

The probe of the device according to the invention is connected to at least one electronic generator. A first wave generator 20 provides and receives a high frequency current from the imaging transducer 12 for a display of the area to be treated by ultrasonography, optionally combined with a Doppler ultrasonography. The signals provided to the imaging transducer are comprised between 5 and 20 MHz. A wave generator 20', separate or integral with the first generator 20, provides power signals to the treatment transducer 11 for a high intensity focussing on the area to be treated. The signals provided to the treatment transducer are comprised between 1 and 5 MHz.

The probe of the device according to the invention is also connected to an electronic processing unit 100 which is able to control the probe 10 and the wave generator 20. In particular, the processing unit 100 can be adapted to interpret the signals received by the imaging transducer 12 in ultrasonograph and/or Doppler mode. The processing unit 100 can also be connected to a man-machine interface 110 for a display of the treated area and/or for an input of operating parameters.

The device according to the invention is intended to treat a given area by high-intensity focussed ultrasound (HIFU). According to the invention, the device makes it possible to focus the ultrasound over a given length. In particular, in the case of treatment of varicose veins, it is particularly useful to produce a high-intensity focussing over a given length of vein surrounding the attachment point of the valve. It is thus possible to avoid the problems of guiding the ultrasound probe along the vein, which is necessary in the case of the standard devices using a point-by-point focussing.

According to the invention, the focal spot of the treatment transducer 11, instead of being punctiform as in most of the known devices, is elongated and inclined with respect to the direction of propagation of the ultrasound, for example over a length of the order of 5 to 10 mm. Moreover, in contrast to the focal line obtained in a standard manner with a cylindrical transducer, the line of the focal spot 6 of the device according to the invention is shorter than the length of the transducer 11, thus guaranteeing a greater concentration of the acoustic intensity. For example, the transducer can have a diameter of the order of 30 to 50 mm for a focal spot of 5 to 10 mm.

For this purpose, the treatment transducer 11 of the device according to the invention has an aspherical surface. In particular, any quadratic surface can be utilized in order to constitute all or part of the transmission surface of the treatment transducer 11.

Depending on the shape and the arrangement of the transducer, the focal spot can be perpendicular or inclined with a larger or smaller angle with respect to the direction of propagation of the waves, for example with an angle of 45° to 90°.

Figure 4A:
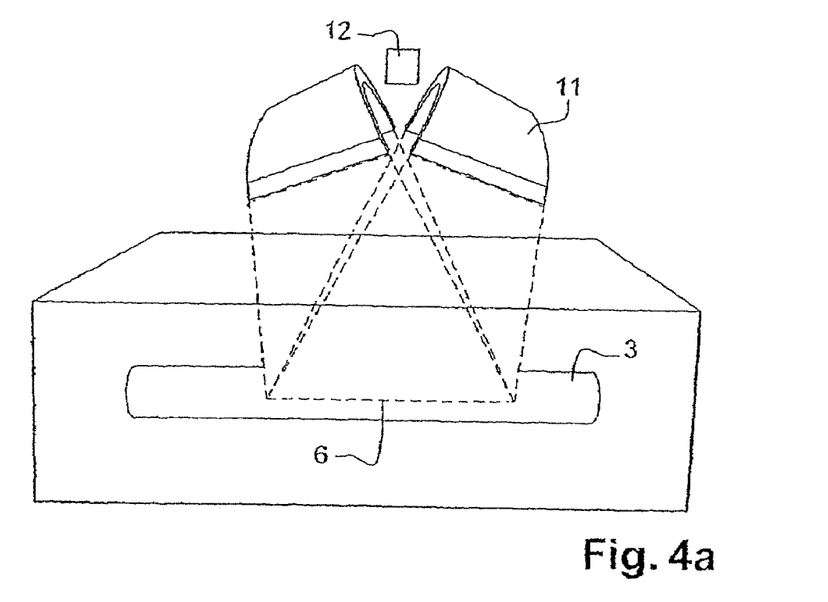
FIGS. 4a to 4c, diagrammatic views, respectively parallel, oblique and perpendicular to the vein, of an ultrasound transducer according to a first embodiment of the device according to the invention.
Figure 4B:
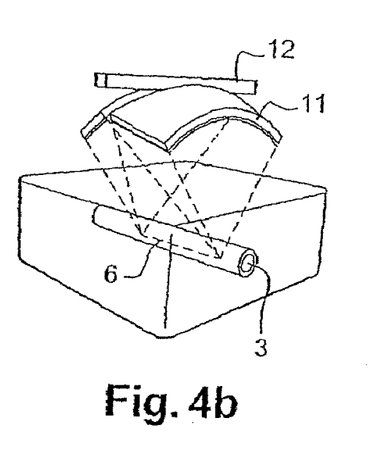
Figure 4C:
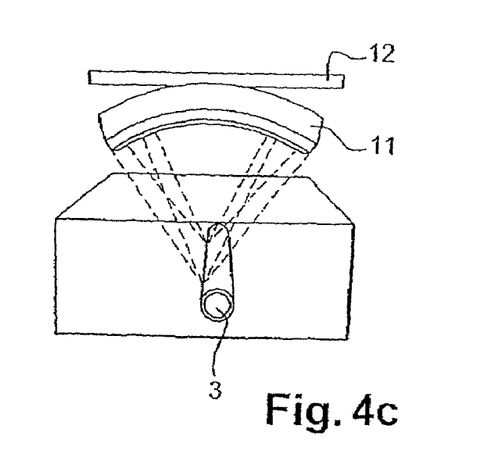

According to a first embodiment, illustrated in FIGS. 4a to 4c, the treatment transducer 11 has a conical transmission surface. The axis of the cone formed by the wavefront of the treatment transducer 11 is merged with the line of the focal spot 6. According to the embodiment illustrated, two conical transducers are arranged in such a way as to focus the ultrasound waves onto the same focal spot 6. The geometry of the transmission surfaces of the treatment transducers and their relative placement are such that the crossing of the beams respectively transmitted produces no cancellation of the waves transmitted by said transducers. The acoustic concentration is thus improved as the two merged focal spots 6 concentrate the ultrasound waves on a line which is very fine and shorter than the length of the assembly of two transducers forming the treatment transducer 11.

The probe integrating the treatment transducer 11 is placed in such a way that the elongated focal spot 6 is in the plane of the vein 3 at the level of the wall presenting a varix. Thus, the dehiscent portion of the vein wall can be heated so as to produce a localized retraction of collagen over this length of vein and close the valve which suppresses blood reflux.

The imaging transducer 12 can be situated at the centre of the treatment transducer 11 and orientated in a manner perpendicular to the major axis of the focal spot 6 in order to observe all of the section of the vein 3. More specifically, the imaging transducer 12 can be placed in the free space between the two treatment transducers 11.

Figure 5A:
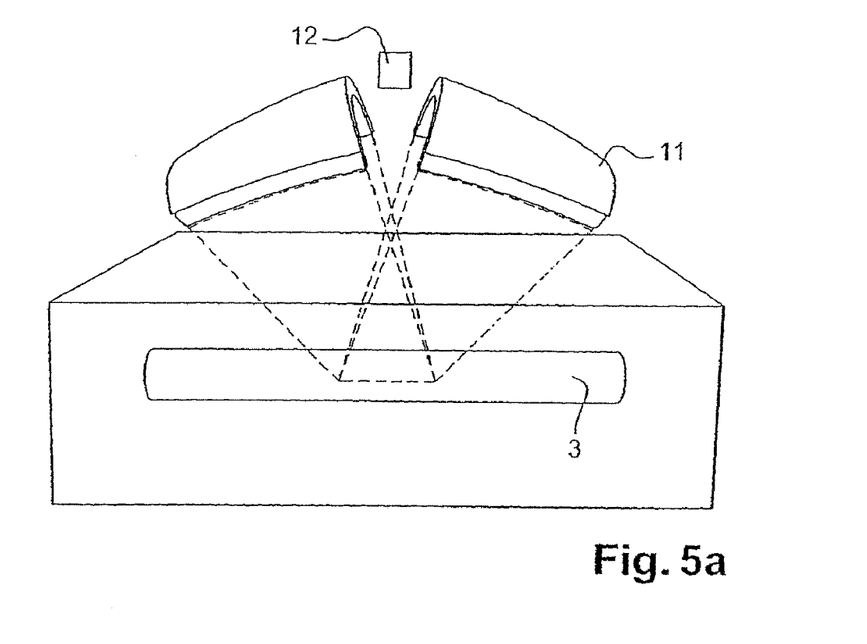
FIGS. 5a to 5c, diagrammatic views, respectively parallel, oblique and perpendicular to the vein, of an ultrasound transducer according to a second embodiment of the device according to the invention.
Figure 5B:
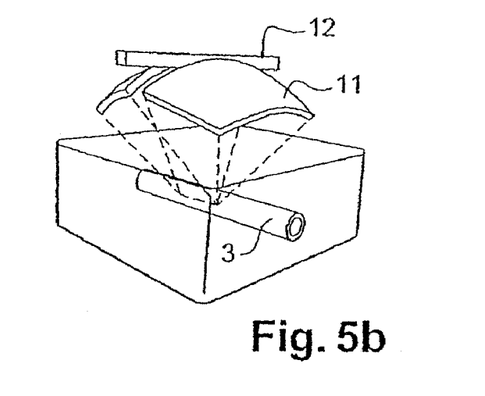
Figure 5C:
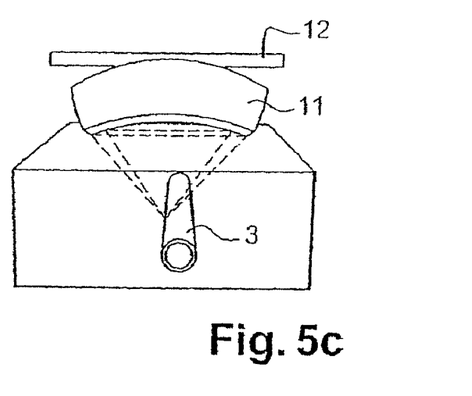

According to a second embodiment, illustrated in FIGS. 5a to 5c, the treatment transducer 11 has an ellipsoid transmission surface. According to the embodiment illustrated, two ellipsoid transducers are arranged so as to focus the ultrasound waves onto the same focal spot 6. According to this embodiment, the geometry of the transmission surfaces of the treatment transducers and their relative placement are also such that the crossing of the beams respectively transmitted does not cause a cancellation of the waves transmitted by said transducers. The acoustic concentration is also improved as the two merged focal spots 6 concentrate the ultrasound waves on a line which is very fine and shorter than each of the transducers forming the treatment transducer 11.

The imaging transducer 12 is situated at the centre of the treatment transducer 11, for example in the space between the two treatment transducers, and orientated in a manner perpendicular to the major axis of the focal spot 6 in order to observe the whole of the section of the vein 3.

Figure 6:
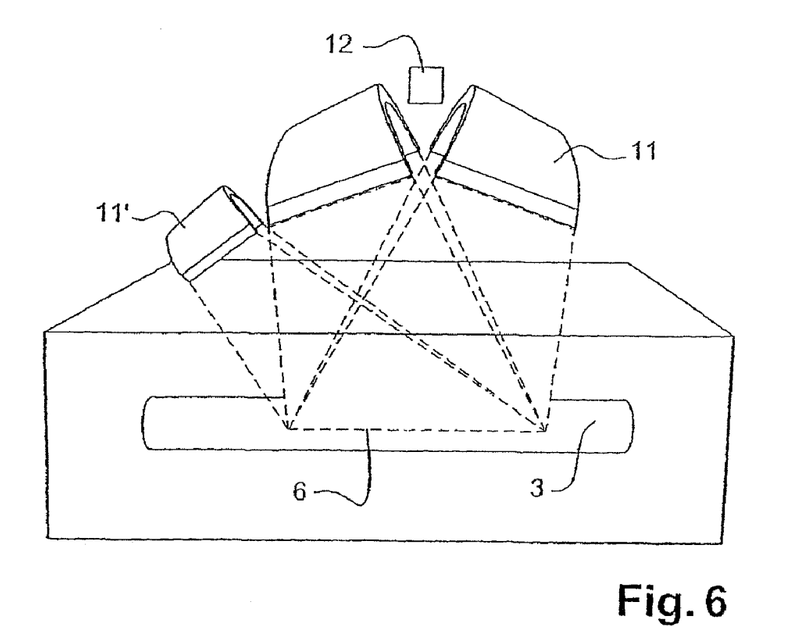
FIG. 6, a diagrammatic view, of ultrasound transducers according to a third embodiment of the device according to the invention.

According to a third embodiment, illustrated in FIG. 6, the treatment transducer assembly comprises two transducers 11 having an ellipsoid wavefront and a transducer 11' having a conical wavefront, the transducers being arranged in such a way as to focus the ultrasound waves onto the same focal spot 6. The relative placement of the transducers and their geometry are such that the crossing of the beams respectively transmitted does not cause a cancellation of the waves transmitted by said transducers. The acoustic concentration is improved as the three merged focal spots 6 concentrate the ultrasound waves on a line which is very fine and shorter than the assembly of the three transducers forming the treatment transducer.

The imaging transducer 12 can be situated between two of the treatment transducers 11 and orientated in a manner perpendicular to the major axis of the focal spot 6 in order to observe the whole of the section of the vein 3.

Figure 7:
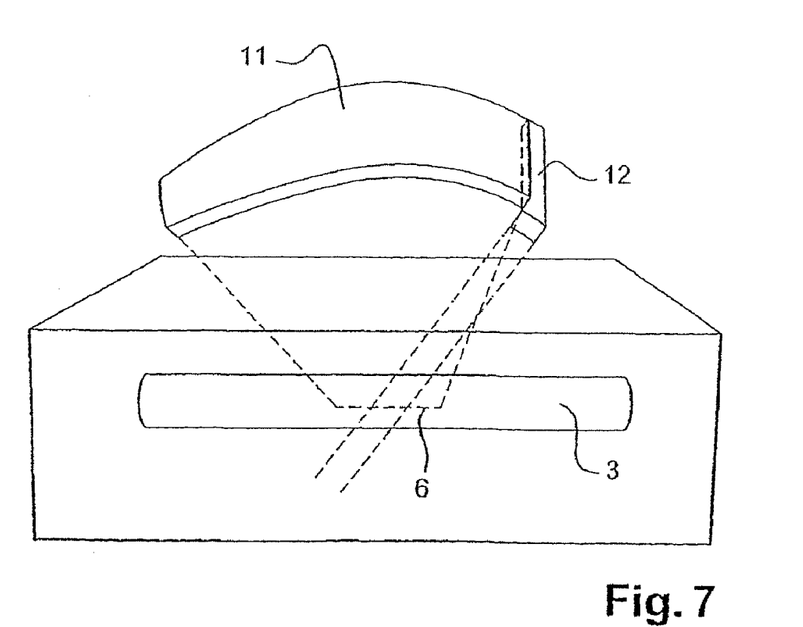
FIG. 7, a diagrammatic view, of ultrasound transducers according to a fourth embodiment of the device according to the invention.

In the embodiment illustrated in FIG. 7, a single treatment transducer 11 having an elliptical wavefront is combined with an imaging transducer 12 orientated in an inclined manner with respect to the major axis of the focal spot 6. Such an orientation of the imaging transducer makes it possible to measure the blood flow in the vein 3 in Doppler mode. The array of the imaging transducer 12 is orientated so as to include in its detection plane a part of the focal line 6, and preferably its centre. Of course, an inclined orientation of the imaging transducer 12 can be combined with any aspherical shape, other than elliptical, of the wavefront of the treatment transducer 11 of the device according to the invention.

The imaging transducer 12 can be integral with the treatment transducer 11. According to one embodiment, the imaging transducer 12 can be mounted on the treatment transducer 11, as illustrated in FIG. 7.

Figure 8:
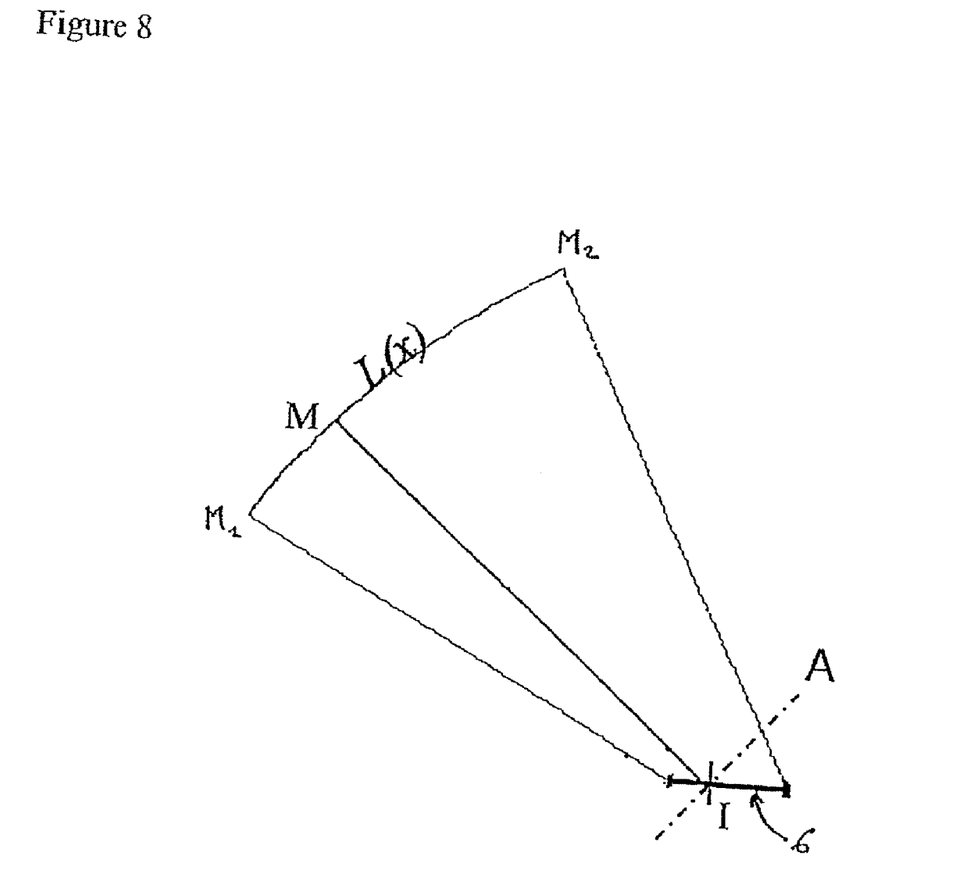
FIG. 8, a diagrammatic representation of a curve serving as the basis for the construction of the wavefront of a transducer according to a fifth embodiment.

According to another embodiment, the aspherical wavefront can be obtained by the following construction method. FIG. 8 illustrates this construction. FIG. 8 shows a curve L(x) serving as a base for the construction of the wavefront of the transducer. The waves intended to be transmitted by this treatment transducer must focus on a spot 6 forming a line and called a focal line.

A curve L(x) is chosen, situated in the mid-plane of the transducers (plane of symmetry of the device), such that all the normals at L(x) intersect the focal line. For each point M of the curve L(x), the intersection of the normal at the curve with the focal line is referred to as I. L(x) is then produced in space; for each point M of the curve L(x) a rotation takes place about the axis A defined as the perpendicular to IM at I. Thus, using each point M, a portion of circle is obtained, the entirety of which forms the surface of one of the transducers. The amplitude of the rotation defines the width of the transducers and is limited by the cutaneous plane. When two transducers are combined as in the examples of FIGS. 4a and 5a, the waves originating from the inside edge of one of the transducers must be prevented from being cancelled out by the waves originating from the outside edge of the other transducer. For this purpose the points of ends Mi and M2 of the curve L(x) will be chosen such that the difference between the distances $M_1I_1$ and $M_2I_2$ is an integer of the wavelengths.

For each transducer, a wavefront is thus obtained, defined as the envelope of a plurality of circles respectively centred on a plurality of points of the focal line and connected to each other in such a way that the two normals at each of the points of the envelope intersect the focal line.

The device according to the invention can be used in the following way.

Firstly, the area to be treated A is located. The superficial vein network of the patient is conventionally explored by Doppler ultrasonography. Such a locating process can be carried out directly with the device according to the invention using the integrated imaging transducer if appropriate or with another device of the ultrasonograph type, optionally provided with a Doppler ultrasonography function.

The patient is generally examined in orthostatism. The search for a reflux can require compression-relaxation movements of the calf.

Exploration by Doppler ultrasonography of the varicose vein(s) searches along the length of this (these) vein(s) for the pathological valve site(s) the precise location of which can be delimited by a cutaneous marking. These sites can be characterized with colour Doppler ultrasonography through the existence of a commissural, partial reflux and/or in B-mode ultrasonography through the existence of a dilatation of the vein wall facing the valve commissure which more or less separates the two leaves of the valve. It is this (these) dilated area(s) of the vein wall that will be recognized as target area(s). This is principally the external edge of the vein wall facing pathological sub-ostial and/or Hunter and/or truncular valves.

The patient is then generally placed in a decubitus position.

The target area(s) of the vein to be treated is (are) precisely identified facing the sites previously identified during the initial Doppler ultrasonography examination.

At each site to be treated, the target area is produced on the screen of the ultrasonograph system. The focussing of the HIFU device is adjusted so as to correspond to the target area.

For example, two treatment transducers are arranged symmetrically relative to the area to be heated and are at sufficient intervals to be able to place an array of an imaging transducer between them. The beams of waves transmitted by the two treatment transducers are concentrated on a line of approximately 7 mm long perpendicular to the image plane of the image transducer. The line of the focal spot is situated in the plane of the vein at a depth, below the skin, of the order of 15 mm. The imaging transducer is placed at most at 10 mm above the skin in order to ensure a good image quality without disturbing the beams of waves transmitted by the treatment transducers.

Before heating, a tumescent local anaesthesia can be carried out by infiltration of a solution of buffered dilute adrenalinated xylocaine into the perisaphenous fascia. In addition to its anaesthetizing effect, this infiltration will compress the vein walls, making a more suitable target for ultrasound.

The power ultrasound is then delivered according to pre-established charts.

The vein wall pathologically dilated at the level of the insertion ring of the valves is heated to an appropriate temperature, for example 75° to 100° C. and preferably 85 to 90° C., for 1 to 60 seconds, preferably 10 to 20 seconds. In this way it is sought to obtain the retraction of the collagen and finally the retraction of the vein wall, without destroying it or the surrounding tissues. The acoustic powers used are of the order of 20 to 35 acoustic W. The ultrasound frequency is of the order of 1 to 5 MHz, preferably of 1.5 to 3 Mhz.

Thus, the invention proposes to treat a varicose pathology by heating the vein wall with focussed ultrasound, without coagulation or occlusion of the vein. The heating is preferably carried out at the level of an insertion ring of a pathological valve.

The effect of each therapeutic sequence can be monitored immediately by Doppler ultrasonography. On the one hand the morphological modifications of the wall are monitored, such as the calibre and the thickness of the wall, and on the other hand the modifications at the hemodynamic level, with the persistence or not of a reflux. If appropriate the power, the intensity or the application time of the ultrasound can be adjusted as a function of this monitoring. It is also possible to monitor the wall by elastography.

One or more additional sequences can be carried out until the valve continence is restored.

Of course, the present invention is not limited to the embodiments described by way of examples; thus, although the treatment transducers 11 have been described with aspherical surfaces, they are equivalent to treatment transducer assemblies having wavefronts with a spherical shape combined with cylindrical lenses, or to treatment transducer assemblies having wavefronts with a flat shape combined with elliptical lenses.

In the above, transducers were described in which the geometry of the transmission surface is identical to the desired shape of the wavefront. For example transducers with a conical shape will transmit a conical wavefront when they are connected to a single electronic generator.

However, the aspherical wavefronts can be obtained from a transducer with any shape, for example spherical or flat, coupled to additional means. According to a first means, an aspherical acoustic lens is inserted between the transducer and the tissue to be treated. According to a second means, the transducer is separated into independent transmission parts which are each connected to a power generator. These generators operate at the same frequency but their phases are shifted so as to obtain the desired wavefront.

The invention claimed is:

1. An ultrasound device comprising a first treatment transducer which can transmit a beam of ultrasound waves to an area to be treated, the beam having an aspherical wavefront and creating a focal spot on the area to be treated, the focal spot being elongated and inclined with respect to the direction of propagation of the ultrasound waves, the length of the focal spot being less than the length of the transducer.

2. An ultrasound device comprising a first treatment transducer which can transmit a beam of ultrasound waves to an area to be treated, the beam having an aspherical wavefront, other than cylindrical, and creating a focal spot on the area to be treated which is elongated and inclined with respect to the direction of propagation of the ultrasound waves.

3. A device according to claim 1 or 2, characterized in that the focal spot is perpendicular to the direction of propagation of the ultrasound waves.

4. A device according to one of claims 1 or 2, comprising a second imaging transducer which is able to display the area to be treated.

5. A device according to claim 4, characterized in that the imaging transducer is able to display a plane perpendicular to a major axis of the focal spot.

6. A device according to claim 4, characterized in that the imaging transducer is able to display a plane inclined with respect to the major axis of the focal spot.

7. A device according to claim 1 or 2, characterized in that the beam of waves transmitted by the treatment transducer has a wavefront with a conical shape.

8. A device according to claim 1 or 2, characterized in that the beam of waves transmitted by the treatment transducer has a wavefront with an ellipsoid shape.

9. A device according to claim 1 or 2, characterized in that the beam of waves transmitted by the treatment transducer has a wavefront with a spherical shape combined with a cylindrical lens.

10. A device according to claim 1 or 2, characterized in that the beam of waves transmitted by the treatment transducer has a wavefront with a flat shape combined with an elliptical lens.

11. A device according to claim 1 or 2, characterized in that the treatment transducer is separated into a plurality of independent parts able to transmit beams of ultrasound waves at the same frequency and phase shifted amongst the beams of ultrasound waves so as to form an aspherical wavefront.

12. A device according to claim 1 or 2, characterized in that the wave beam transmitted by the treatment transducer has a wavefront defined as an envelope of a plurality of circles respectively centred on a plurality of points of the focal spot and connected to each other in such a way that two normals at each point of the envelope intersect a focal line.

13. A device according to claim 1 or 2, comprising a plurality of treatment transducers which are able to focus beams of ultrasound waves onto the same focal spot on an area to be treated.

14. A device according to claim 4, characterized in that the imaging transducer is integral with the treatment transducer.

15. A device according to claim 4, comprising control means for the frequency and/or the power of the ultrasound waves transmitted by the first treatment transducer and/or the duration of transmission of the ultrasound waves onto a surface to be treated.

16. A device according to claim 15, characterized in that the control means are able to interpret data provided by the imaging transducer.

17. Method for the transmission of ultrasound onto an area to be treated comprising the stages of:
   transmitting a beam of ultrasound waves having an aspherical wavefront by a treatment transducer;
   focussing the ultrasound waves according to an elongated focal spot shorter than a length of the treatment transducer and inclined with respect to the direction of propagation of the ultrasound waves.

18. Method according to claim 17, comprising a stage of locating the area to be treated by Doppler ultrasonography.

19. Method according to claim 17 or 18, comprising a stage of displaying the treated zone.

20. Method according to claim 19, characterized in that the stages of transmission and/or focussing of the ultrasound waves are monitored by displaying the treated zone.

21. A method for treating a vein wall, the method comprising subjecting an area to be treated comprising the vein wall with abeam of ultrasonic waves transmitted from an ultrasound device, the ultrasonic device comprising a first treatment transducer transmitting the beam to the area to be treated, the beam having an aspherical wavefront and creating a focal spot on the area to be treated, the focal spot being elongated and inclined with respect to a direction of propagation of the ultrasound waves, a length of the focal spot being less than a length of the transducer.

22. A method for treating a solid tumour, the method comprising subjecting an area to be treated with a beam of ultrasonic waves transmitted from an ultrasound device, the ultrasonic device comprising a first treatment transducer transmitting the beam to the area to be treated, the beam having an aspherical wavefront and creating a focal spot on the area to be treated, the focal spot being elongated and inclined with respect to the direction of propagation of the ultrasound waves a length of the focal spot being less than a length of the transducer.

* * * * *

UNITED STATES PATENT AND TRADEMARK OFFICE
CERTIFICATE OF CORRECTION

| | |
|---|---|
| PATENT NO. | : 7,713,203 B2 |
| APPLICATION NO. | : 11/572465 |
| DATED | : May 11, 2010 |
| INVENTOR(S) | : Lacoste et al. |

Page 1 of 1

It is certified that error appears in the above-identified patent and that said Letters Patent is hereby corrected as shown below:

Column 12, line 6, delete "abeam" and insert therefor --a beam--.
Column 12, line 23, after "waves", insert --,--.

Signed and Sealed this

Twenty-ninth Day of June, 2010

David J. Kappos
*Director of the United States Patent and Trademark Office*